(12) United States Patent
Kulstad et al.

(10) Patent No.: US 12,290,470 B2
(45) Date of Patent: May 6, 2025

(54) REINFORCED ESOPHAGEAL HEAT TRANSFER DEVICES

(71) Applicant: Advanced Cooling Therapy, Inc., Chicago, IL (US)

(72) Inventors: Erik Kulstad, Dallas, TX (US); Frank E. Garrett, Jr., Barrington, IL (US)

(73) Assignee: Advanced Cooling Therapy, Inc., Chicago, IL (US)

( * ) Notice: Subject to any disclaimer, the term of this patent is extended or adjusted under 35 U.S.C. 154(b) by 0 days.

(21) Appl. No.: 18/462,339

(22) Filed: Sep. 6, 2023

(65) Prior Publication Data

US 2024/0164940 A1 May 23, 2024

Related U.S. Application Data

(63) Continuation of application No. 16/498,263, filed as application No. PCT/US2018/024493 on Mar. 27, 2018, now abandoned.

(60) Provisional application No. 62/480,842, filed on Apr. 3, 2017, provisional application No. 62/477,012, filed on Mar. 27, 2017.

(51) Int. Cl.
*A61F 7/12* (2006.01)
*A61F 7/00* (2006.01)

(52) U.S. Cl.
CPC ........ *A61F 7/12* (2013.01); *A61F 2007/0054* (2013.01)

(58) Field of Classification Search
CPC ............................ A61F 2007/0054; A61F 7/12
See application file for complete search history.

(56) References Cited

U.S. PATENT DOCUMENTS

| | | |
|---|---|---|
| 5,441,516 A | 8/1995 | Wang et al. |
| 6,694,977 B1 | 2/2004 | Federowicz et al. |
| 2003/0078638 A1 | 4/2003 | Voorhees et al. |
| 2003/0088240 A1 | 5/2003 | Saadat |

(Continued)

FOREIGN PATENT DOCUMENTS

| | | |
|---|---|---|
| WO | 1999/05996 A1 | 2/1999 |
| WO | 2018/183278 A1 | 10/2018 |

OTHER PUBLICATIONS

The United Stated Patent and Trademark Office, International Search Report in International Application No. PCT/US18/24493 (Jun. 21, 2018).

(Continued)

*Primary Examiner* — Kaitlyn E Smith
(74) *Attorney, Agent, or Firm* — Nutter McClennen & Fish LLP

(57) ABSTRACT

Reinforced esophageal heat transfer devices are disclosed. An example reinforced esophageal heat transfer device includes a distal end configured for nasopharyngeal or oropharyngeal insertion into an esophagus of a subject, a proximal end including an inlet port and an outlet port, a heat transfer region between the distal end and the proximal end, one or more lumens configured for providing a fluid path for flow of a heat transfer medium to and from the heat transfer region, and one or more reinforcing elements configured for reinforcing the one or more lumens to enable the heat transfer medium to flow through the fluid path via negative pressure.

5 Claims, 3 Drawing Sheets

(56) References Cited

U.S. PATENT DOCUMENTS

| | | | |
|---|---|---|---|
| 2004/0210286 A1* | 10/2004 | Saadat | A61F 7/12 |
| | | | 607/113 |
| 2006/0175543 A1 | 8/2006 | Elefteriades | |
| 2007/0225781 A1 | 9/2007 | Saadat et al. | |
| 2008/0161890 A1 | 7/2008 | Lafontaine | |
| 2009/0005725 A1 | 1/2009 | Shorey | |
| 2011/0029050 A1 | 2/2011 | Elefteriades et al. | |
| 2012/0197245 A1 | 8/2012 | Burnett et al. | |
| 2013/0006336 A1 | 1/2013 | Kulstad et al. | |
| 2013/0231584 A1 | 9/2013 | Burnett et al. | |
| 2014/0018618 A1* | 1/2014 | Mitelberg | A61B 1/00135 |
| | | | 600/114 |
| 2014/0277305 A1* | 9/2014 | Kulstad | A61N 1/39 |
| | | | 607/113 |
| 2014/0371736 A1 | 12/2014 | Levin et al. | |
| 2015/0282858 A1 | 10/2015 | Baust et al. | |
| 2016/0354144 A1* | 12/2016 | Caplan | A61B 18/1492 |

OTHER PUBLICATIONS

The United Stated Patent and Trademark Office, Written Opinion in International Application No. PCT/US18/24493 (Jun. 21, 2018).

European Patent Office, Supplementary European Search Report in Application No. EP 18774511 (Nov. 18, 2020).

U.S. Appl. No. 16/498,263, filed Sep. 26, 2019.

Office Action for U.S. Appl. No. 16/498,263 dated Jun. 20, 2022, 25 pages.

Office Action for U.S. Appl. No. 16/498,263 dated Mar. 6, 2023, 23 pages.

Extended European Search Report and Written Opinion for application No. 18774511.2 PCT/US2018/024493 dated Nov. 18, 2020, 11 pages.

* cited by examiner

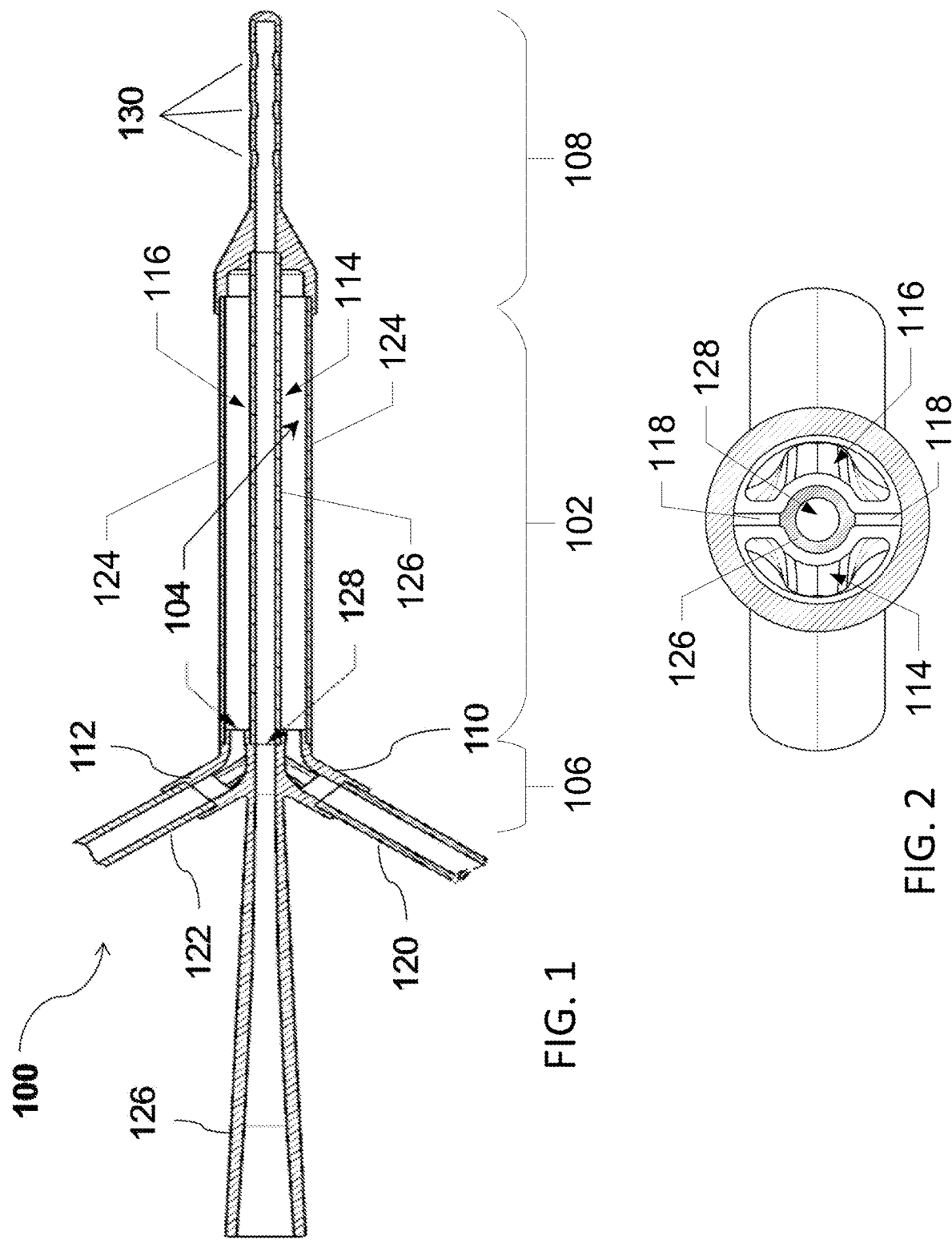

REINFORCED ESOPHAGEAL HEAT TRANSFER DEVICES

RELATED APPLICATIONS

The present application is a continuation of U.S. patent application Ser. No. 16/498,263, filed Sep. 26, 2019, which is a national phase application under 35 U.S.C. 371 of International Application No. PCT/US2018/024493, filed on Mar. 27, 2018, which claims priority to U.S. Provisional Patent Application No. 62/477,012, filed on Mar. 27, 2017 and 62/480,842, filed on Apr. 3, 2017. The contents of each of the aforementioned applications are incorporated herein by reference in its entirety

TECHNICAL FIELD

The present disclosure generally relates to heat transfer devices, more specifically, reinforced esophageal heat transfer devices; systems; and methods for managing temperature, particularly esophageal temperature and/or core body temperature, in a subject. In one aspect, the present technology relates to a reinforced esophageal heat transfer device for managing core body temperature in a subject. In one aspect, the present technology relates to a temperature management system including a reinforced esophageal heat transfer device for managing core body temperature in a subject. In one aspect, the present technology relates to a method of using a reinforced esophageal heat transfer device or temperature management system for managing core body temperature in a subject.

BACKGROUND

Active temperature management has been shown to be important for a number of conditions. In particular, adults who remain comatose after resuscitation from cardiac arrest, neonates suffering from hypoxic ischemic encephalopathy, and patients undergoing general surgical procedures longer than one hour in duration all have strong recommendations for temperature modulation. More broadly, active temperature management has been shown to be potentially beneficial for certain subsets of traumatic brain injury, including refractory fever in acutely brain injured patients; spinal cord injury; certain subsets of stroke; acute myocardial infarction; traumatic/hemorrhagic cardiac arrest; surgical operations lasting longer than one hour; hepatic encephalopathy; sepsis/septic shock; and raised intracranial pressure.

For example, temperature management in an operative setting may improve patient outcome and reduce adverse events. Oftentimes, a patient's body temperature is controlled while undergoing surgical procedures in an operating room. The patient's body temperature may be controlled to avoid perioperative hypothermia during operative procedures, which potentially may otherwise increases the incidence of wound infection, prolong hospitalization, increase the incidence of morbid cardiac events and ventricular tachycardia, and/or impair coagulation. In some instances, surface cooling (e.g., via blankets, external vests, cooling helmets, etc.), raised operating room temperatures, inhaled gases, balloon catheters, and/or intravenous fluids are utilized to control a patient's body temperature during surgery.

Circulation of heat transfer medium (e.g., water, saline, etc.) within an esophageal heat transfer device allows for management of core body temperature of a subject. External heat exchangers are used to monitor subject temperature and adjust the temperature of circulating heat transfer medium to warm the subject, cool the subject, and/or maintain the subject at a relatively constant temperature, such as in a state of normothermia. Available esophageal heat transfer devices are fabricated from relatively thin-walled silicone tubing, which has a desirable combination of heat transfer, manufacturability, and strength properties.

SUMMARY

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

In one aspect, the present technology pertains to a reinforced esophageal heat transfer device. An example disclosed reinforced esophageal heat transfer device includes a distal end configured for nasopharyngeal or oropharyngeal insertion into an esophagus of a subject, a proximal end including an inlet port and an outlet port, a heat transfer region between the distal end and the proximal end and configured for contacting esophageal epithelium of the subject, a flexible tube defining one or more lumens configured for providing a fluid path for flow of a heat transfer medium to and from the heat transfer region, and one or more reinforcing elements, such as a reinforcing wire (e.g., a coiled wire), configured for reinforcing the flexible tube to enable the heat transfer medium to flow through the fluid path via negative pressure.

In one aspect, the present technology pertains to an esophageal heat transfer device comprising at least one reinforced silicone tube. In certain embodiments, the reinforced silicone tube comprises at least one reinforcing element. In certain embodiments, the reinforcing element is a reinforcing wire. In certain embodiments, the reinforcing element is a reinforcing coil. In certain embodiments, the reinforcing coil is a metal spring, such as a stainless steel spring, a nylon spring, or a plastic spring. In certain embodiments, the reinforcing coil is coextruded with the silicone during the formation of the tube itself. In certain embodiments, the reinforcing coil has a substantially D-shaped cross section. In other embodiments, the reinforcing coil has a circular cross section such that the coil is substantially cylindrical. In certain embodiments, the reinforcing coil is a light weight, low stiffness compression spring. In certain embodiments, the reinforcing coil has a diameter of about 1 mm to about 5 mm, preferably about 3 mm.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

FIG. 1 is a cross-sectional side view an example heat transfer device in accordance with the teachings herein.

FIG. 2 is a cross-sectional view the example heat transfer device of FIG. 1.

DETAILED DESCRIPTION

Figures 3A, 3B:
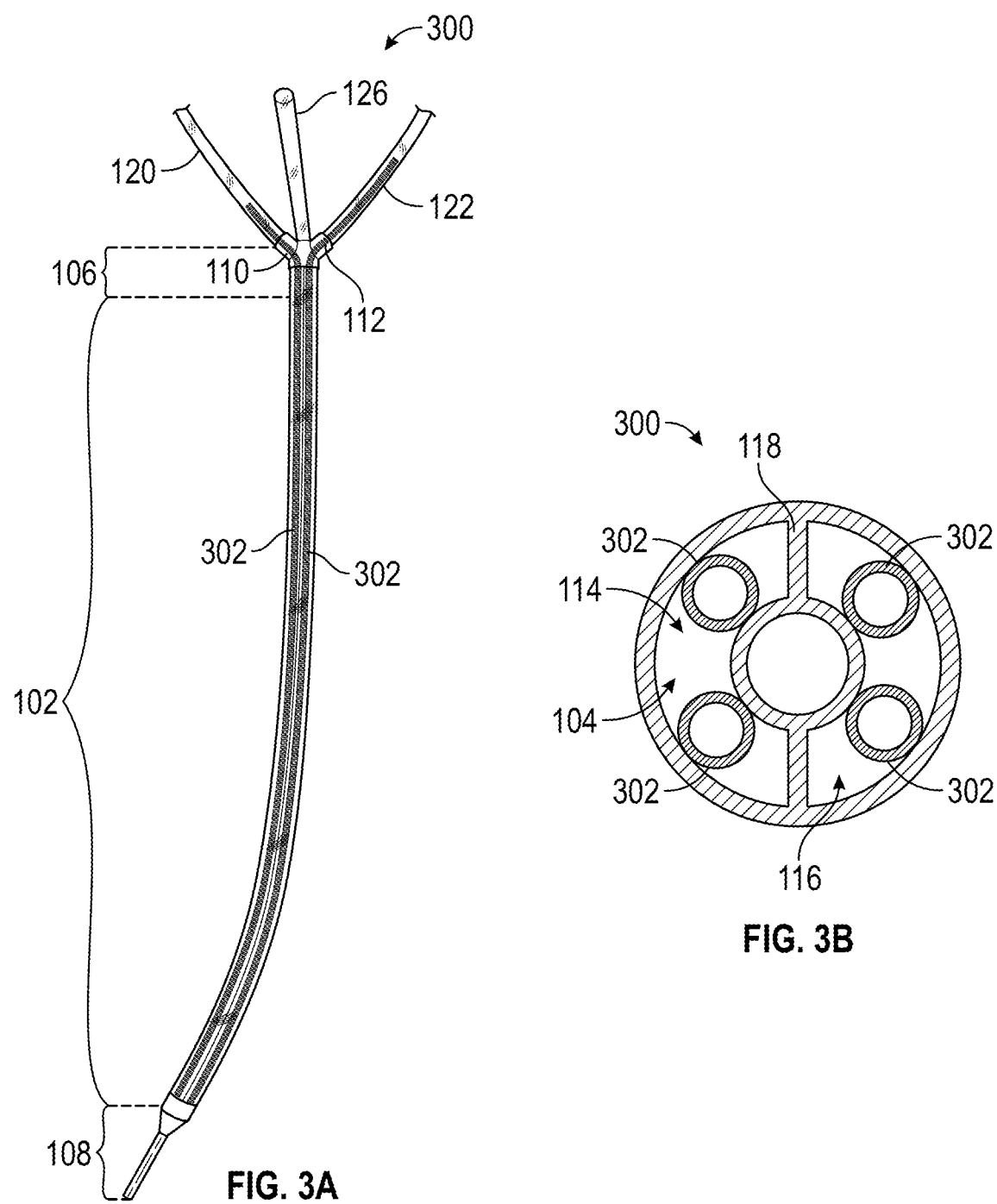
FIG. 3A depicts another example heat transfer device in accordance with the teachings herein.
FIG. 3B is a cross-sectional view of the heat-transfer device of FIG. 3A.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

Oftentimes, a patient's body temperature is controlled while undergoing surgical procedures in an operating room. The patient's body temperature may be controlled to avoid perioperative hypothermia during operative procedures, which potentially may otherwise increases the incidence of wound infection, prolong hospitalization, increase the incidence of morbid cardiac events and ventricular tachycardia, and/or impair coagulation. In some instances, surface cooling (e.g., via blankets, external vests, cooling helmets, etc.), raised operating room temperatures, inhaled gases, balloon catheters, and/or intravenous fluids are utilized to control a patient's body temperature during surgery.

In one aspect, the present technology pertains to a reinforced esophageal heat transfer device. Example reinforced esophageal heat transfer devices include a heat transfer region that is configured for contacting tissue (e.g., esophageal epithelium) of a subject and transferring heat to the esophageal epithelium to heat or cool the subject. In certain embodiments, the reinforced esophageal heat transfer devices include a distal end configured for nasopharyngeal or oropharyngeal insertion into an esophagus of the subject and a proximal end that includes an inlet port and an outlet port. In some such embodiments, the heat transfer region is located between the distal end and the proximal end. Further, an example reinforced esophageal heat transfer device includes a plurality of lumens (e.g., a heat transfer medium supply lumen, a heat transfer medium return lumen) that are configured for providing a fluid path for flow of a heat transfer medium to and from the heat transfer region. Example reinforced esophageal heat transfer devices include a reinforcing element. For example, a plurality of reinforcing wires are configured for reinforcing a flexible tube that defines the plurality of lumens to enable the heat transfer medium to flow through the fluid path via negative pressure. That is, the example reinforced esophageal heat transfer devices are reinforced with the plurality reinforcing wires to prevent the negative pressure from collapsing the flexible tube and, thus, maintain the patency of the fluid path.

In certain embodiments, the reinforcing element is integrated with the device and, in particular, the flexible tube(s) defining a lumen for flow of heat transfer medium. For example, the reinforcing element may be coextruded with the tubing during the formation of the tube itself. In certain embodiments, the reinforcing element is a separate component from the device. For example, the reinforcing element may be disposed within the lumen.

In certain embodiments disclosed herein, a reinforced esophageal heat transfer device is intended to control a subject's temperature, while simultaneously maintaining access to the stomach to allow gastric decompression and drainage. In some such embodiments, the esophageal heat transfer device comprises a silicone tube with three lumens. In some such embodiments, two parallel lumens (an inflow lumen and an outflow lumen) are in fluid communication with each other and an external heat exchanger to provide a fluid path for the flow of heat transfer medium to and from the external heat exchanger. In some such embodiments, a third lumen provides gastric access. The third lumen can be connected to wall suction and used for standard gastric decompression. In certain embodiments, the third lumen is in a co-axial arrangement with the inflow and outflow lumens. In some such embodiments, a web supports the inner gastric lumen and separates inflow and outflow lumens. Upon placement in a subject, an external portion of the silicone tube is in contact with the esophageal tissue of the subject. Modulation and control of subject temperature is intended to be achieved by connecting the device to an external heat exchanger and circulating temperature-controlled heat transfer medium (e.g., water) along the fluid path.

In one aspect, the present technology pertains to an esophageal heat transfer device comprising at least one reinforced silicone tube. In certain embodiments, the reinforced silicone tube comprises at least one reinforcing element. The reinforcing element enhances the radial stiffness of the tube sufficiently to prevent the collapsing of the tube when operating in a negative pressure environment and/or enhances longitudinal stiffness of the tube to enhance placement. In certain embodiments, the reinforcing element is a light weight, low stiffness compression spring. In certain embodiments, the spring is a metal spring. In certain embodiments, the metal is non-ferromagnetic metal. In certain embodiments, one or more such springs are disposed within at least one lumen of the esophageal heat transfer device (i.e., multiple springs may be present in each lumen). In certain embodiments, a single spring is coextruded to maintain the stiffness of the tube. In certain embodiments, an exemplary esophageal heat transfer device comprises three lumens: inflow lumen, outflow lumen, and central lumen. In some such embodiments, at least one reinforcing element is disposed within at least one of the lumens. In some such embodiments, the reinforcing element is a reinforcing wire, such as metal spring. In some such embodiments, a first metal spring is disposed within the inflow lumen and a second metal spring is disposed within the outflow lumen. In some such embodiments, a first set of metal springs are disposed within inflow lumen and a second set of metal springs are disposed within the outflow lumen. The first set of metal springs can be arranged in parallel to each other. Likewise, the second set of metal springs can be arranged in parallel to each other. In some such embodiments, extension tubes are provided to connect the heat transfer device to an external heat exchanger.

In certain embodiments, an esophageal heat transfer device comprising at least one reinforced silicone tube has an increased radio-opacity relative to existing esophageal heat transfer devices. As such, an esophageal heat transfer device comprising at least one reinforced silicone tube may be viewed using x-ray imaging.

In certain embodiments, the reinforcing element is integrated with the device and, in particular, the silicone tube. For example, the reinforcing element may be coextruded with the silicone during the formation of the tube itself. In certain embodiments, the reinforcing element is a separate component from the device. For example, the reinforcing element may be disposed within the lumen of the silicone tube.

In one aspect, the present technology pertains to a system to manage temperature in a subject, the system including: an esophageal heat transfer device comprising at least one reinforced silicone tube and a source of a heat transfer medium. The esophageal heat transfer device is capable of interconnection to the source of the heat transfer medium. The source of the heat transfer medium operates to circulate the heat transfer medium through the heat transfer device. In certain embodiments, the source of the heat transfer medium includes a reservoir. In certain embodiments, the reservoir is capable of storing the heat transfer medium. In certain embodiments, the system includes the esophageal heat transfer device comprising at least one reinforced silicone tube and a negative pressure chiller, such as the Arctic Sun Temperature Management System (Bard Medical) or equivalent unit In certain embodiments, the esophageal heat transfer device comprising at least one reinforced silicone tube is used with a negative pressure chiller, such as the Arctic Sun Temperature Management System (Bard Medical) or equivalent unit. In certain other embodiments, the esophageal heat transfer device comprising at least one reinforced silicone tube is used with another source of heat transfer medium such as a Medi-Therm III Conductive Hyper/Hypothermia System (Gaymar/Stryker), a Blanketrol II or Blanketrol III Hyper-Hypothermia System (Cincinnati Sub-Zero) or equivalent unit.

In certain embodiments, the source of the heat transfer medium supplies temperature-controlled fluid, such as water or saline, through a connector hose to the heat transfer device. An accessory temperature probe may interface between the source and the subject to sense subject temperature, which may be displayed on the source's control panel. In certain embodiments, the source includes a circulating pump, heater, and refrigeration system.

In certain embodiments, the system further comprises a subject temperature probe. In certain embodiments, the source of the heat transfer medium interfaces with a subject temperature probe. The subject temperature probe can be a component of the heat transfer device or a separate device that is capable of being directly or indirectly coupled to the source. Subject temperature probes are commercially available from, for example, Smiths Medical. Subject temperature probes are available for rectal, oral, vaginal, esophageal, or bladder temperature measurement.

In certain embodiments, the system includes: (a) at least one processor; (b) at least one operator interface configured to provide input to the processor; and (c) at least one memory. The system is configured to: (1) receive an operator generated temperature setting and (2) control the temperature of the heat transfer medium and/or the flow rate of heat transfer medium through the heat transfer device.

In certain embodiments, the system senses a temperature of the subject (e.g., core body temperature of the subject) through a temperature probe and compares it to a user-selected target temperature, adjusting the temperature and/or flow rate of the heat transfer medium appropriately. For example, a temperature probe may convert subject temperature data into electronically readable signals that are transmitted to the source of the heat transfer medium, which then, if necessary, automatically adjusts the temperature and/or flow rate of the heat transfer medium to achieve target temperature.

In certain embodiments, the reinforcing element enhances radial stiffness of the tube sufficiently to prevent the collapsing of the tube when operating under negative pressure. In certain embodiments, the reinforcing element additionally provides longitudinal stiffness to the device. The additional longitudinal stiffness provided by the reinforcing element allows for easier placement of the device. In certain embodiments, the reinforcing element provides sufficient longitudinal stiffness to facilitate insertion and placement of the device, but also includes sufficient flexibility to facilitate traversal of the subject's pharynx and esophagus from an access point, such as the subject's mouth or nostril. In certain embodiments, the term "subject" includes a mammal in need of therapy for a condition, disease, or disorder or the symptoms associated therewith. The term "subject" includes dogs, cats, pigs, cows, sheep, goats, horses, rats, mice and humans. The term "subject" does not exclude an individual that is normal in all respects.

In certain embodiments, the subject is in need of targeted temperature management. In certain embodiments, the subject is febrile. In some such embodiments, the subject is in an intensive care unit. In certain embodiments, the subject is suffering from or is at risk of suffering an ischemia-reperfusion injury.

In certain embodiments, the subject presents with out-of-hospital cardiac arrest (OHCA). In certain embodiments, the subject presents with in-hospital cardiac arrest (IHCA). In certain embodiments, the subject has been resuscitated following cardiac arrest. In some such embodiments, the subject's core body temperature is maintained between about 33° C. and about 36° C., such as about 33° C., about 34° C., about 35° C., or about 36° C., for at least 12 hours. Alternatively, the subject's core body temperature is maintained between about 33° C. and about 36° C. for at least 24 hours, at least 36 hours, at least 48 hours, at least 60 hours, at least 72 hours, at least 84 hours, or at least 96 hours.

In certain embodiments, the subject has hypoxic ischemic encephalopathy. In some such embodiments, the subject's core body temperature is maintained between about 32° C. and about 34° C., such as about 32° C., about 33° ° C., or about 34° C., for at least 24 hours. Alternatively, the subject's core body temperature is maintained between about 32° C. and about 34° C. for at least 48 hours, at least 72 hours, or at least 96 hours.

In certain embodiments, the subject has suffered a neurological insult, such as a stroke, spinal cord injury, or traumatic brain injury. In some such embodiments, the subject's core body temperature is maintained at normothermia for at least 24 hours. Alternatively, the subject's core body temperature is maintained at normothermia for at least 48 hours, at least 72 hours, or at least 96 hours.

In certain embodiments, the subject has suffered an acute myocardial infarction. In some such embodiments, the subject's core body temperature is maintained between about 33° C. and about 36° C., such as about 33° C., about 34° C., about 35° C., or about 35° C., for at least 12 hours. Alternatively, the subject's core body temperature is maintained between about 33° C. and about 36° C. for at least 24 hours, at least 36 hours, at least 48 hours, at least 60 hours, at least 72 hours, at least 84 hours, or at least 96 hours.

In certain embodiments, the subject is a burn patient. In some such embodiments, the burn patient is undergoing a surgical procedure. In some such embodiments, the burn patient's core body temperature is maintained at normothermia for the duration of the surgical procedure. In some such embodiments, the burn patient's core body temperature is maintained within a target range for the duration of the surgical procedure.

In certain embodiments, the subject is a patient undergoing a surgical operation. In some such embodiments, the surgical operation is scheduled to last for more than one, two, three, four, five, six, seven, or eight hours. In a particular embodiment, the surgical operation is scheduled to last for at least one hour. In some such embodiments, the subject's core body temperature is maintained at normothermia for the duration of the surgical operation. In some such embodiments, the subject's core body temperature is maintained within a target range for the duration of the surgical operation.

Turning to the figures, FIGS. 1 and 2 depict an exemplary reinforced heat transfer device 100 in accordance with the teachings herein. More specifically, FIG. 1 is a cross-sectional side view of the reinforced heat transfer device 100, and FIG. 2 is a cross-sectional view of the heat transfer region of the reinforced heat transfer device 100.

As illustrated in FIG. 1, the reinforced heat transfer device 100 includes a heat transfer region 102, which includes an internal cavity 104. The reinforced heat transfer device 100 includes a proximal end 106 and a distal end 108. The heat transfer region 102 extends between the proximal end 106 and the distal end 108. The reinforced heat transfer device 100 also includes an inlet port 110 and an outlet port 112. The inlet port 110 is fluidly connected to a heat transfer medium supply lumen 114 of the reinforced heat transfer device 100, and the outlet port 112 is fluidly connected to a heat transfer medium return lumen 116 of the reinforced heat transfer device 100.

As illustrated in FIG. 2, the reinforced heat transfer device 100 includes a wall 118 that divides the internal cavity 104 into a multi-lumen cavity including the heat transfer medium supply lumen 114 and the heat transfer medium return lumen 116. The heat transfer medium supply lumen 114 and the heat transfer medium return lumen 116 are in fluid communication with each other, thereby defining a fluid path for flow of a heat transfer medium through the reinforced heat transfer device 100. For example, the wall 118 extends from the proximal end 106 and toward, but not to, the distal end 108 such that the heat transfer medium supply lumen 114 and the heat transfer medium return lumen 116 fluid connected toward the distal end 108 of the reinforced heat transfer device 100.

Returning to FIG. 1, the inlet port 110 is configured to connect to an inflow tube 120, and the outlet port 112 is configured to connect to an outflow tube 122. For example, the inflow tube 120 and the outflow tube 122 are coupled to an external source (e.g., a heat exchanger configured to heat or chill a heat transfer medium). The inflow tube 120 defines an external supply lumen that provides a fluid path for flow of the heat transfer medium from the heat exchanger and to the heat transfer medium supply lumen 114 of the reinforced heat transfer device 100. The outflow tube 122 defines an external return lumen that provides a fluid path for flow of the heat transfer medium from the heat transfer medium return lumen 116 of the reinforced heat transfer device 100 to the external source.

When the external source is a heat exchanger, the heat exchanger may be any of a variety of conventionally designed heat exchangers. For example, the heat exchanger may operate to provide the heat transfer medium via negative pressure. The heat transfer medium may be a gas, such as, for example, nitrous oxide, Freon, carbon dioxide, or nitrogen. Alternatively, the heat transfer medium may be a liquid, such as, for example, water, saline, propylene glycol, ethylene glycol, or mixtures thereof. In other embodiments, the heat transfer medium may be a slurry, such as, for example, a mixture of ice and salt. In still other embodiments, the heat transfer medium may be a gel, such as, for example, a refrigerant gel. Alternatively, the heat transfer medium may be a solid, such as, for example, ice or a heat conducting metal. In other embodiments, the heat transfer medium may be formed, for example, by mixing a powder with a liquid. Thus, it should be understood that combinations and/or mixtures of the above-mentioned media may be employed to achieve a heat transfer medium according to the present technology.

Thus, the inflow tube 120 and the outflow tube 122 fluidly connect the heat exchanger and the reinforced heat transfer device 100 to enable the heat transfer medium to flow between the heat exchanger and the reinforced heat transfer device 100 to heat or cool the reinforced heat transfer device 100. For example, when the inflow tube 120 is coupled to the inlet port 110 and the outflow tube 122 is coupled to the outlet port 112, the heat transfer medium flows from the heat exchanger, through the inflow tube 120 and into the heat transfer medium supply lumen 114 to heat or cool a subject via the heat transfer medium. Further, the heat transfer medium flows from the heat transfer medium supply lumen 114, through the heat transfer medium return lumen 116, and to the outflow tube 122 to circulate the heat transfer medium back to the heat exchanger.

Additionally, the reinforced heat transfer device 100 is configured for placement within an anatomical structure of a mammalian subject. The distal end 108 of the reinforced heat transfer device 100 is configured for insertion into a body orifice. For example, the distal end 108 of the reinforced heat transfer device 100 is configured for insertion into the nostrils, mouth, anus, or urethra of a subject. When properly inserted, the distal end 108 of the reinforced heat transfer device 100 may be ultimately positioned in the esophagus, rectum, colon, bladder, or other anatomical structure. Upon insertion of the reinforced heat transfer device 100 into a subject (e.g., via nostrils, mouth, anus, or urethra), a heat transfer region 102 of the reinforced heat transfer device 100 may directly contact an epithelial surface of the subject. For example, when the reinforced heat transfer device 100 is inserted into an esophagus of the subject, at least a portion of the heat transfer region 102 directly contacts the esophageal epithelium of the subject. For example, the heat transfer region 102 may comprise flexible tubing 124 and is generally located between the distal end 108 and the proximal end 106. In other examples, the heat transfer region 102 is defined by the flexible tubing 124 and the distal end 108 of the reinforced heat transfer device 100. The heat transfer medium is supplied to the reinforced heat transfer device 100 (e.g., from a heat exchanger) via the inlet port 110 and the inflow tube 120 connected to the inlet port 110. The heat transfer medium circulates through the reinforced heat transfer device 100 to transfer heat (e.g., to heat, to cool, or to maintain temperature) between the subject and the heat transfer region 102 that contacts and/or is positioned adjacent to an inner surface (e.g., of the esophagus) of the subject. Further, the heat transfer medium exits the reinforced heat transfer device 100 through the outlet port 112 and the outflow tube 122 connected to the outlet port 112.

As illustrated in FIGS. 1 and 2, the reinforced heat transfer device 100 also includes a gastric access tube 126 that defines a gastric access lumen 128 and extends to the distal end 108 of the reinforced heat transfer device 100.

Further, the reinforced heat transfer device 100 includes one or more ports 130 along the side of the gastric access tube 126. In the illustrated example, the one or more ports 130 are located along the gastric access tube 126 at the distal end 108 of the reinforced heat transfer device 100. The one or more ports 130 may provide for communication between the space exterior to the reinforced heat transfer device 100 and the gastric access lumen 128. For example, the one or more ports 130 may act as a portal between the subject's stomach and the gastric access lumen 128 allowing the gastric contents to be suctioned from the subject's stomach out through the gastric access lumen 128. The presence of one or more ports 130 provides reduced likelihood of blockage of the gastric access lumen 128 from semi-solid stomach contents. Alternatively, multiple gastric access lumens may be employed. The addition of one or more ports 130 may improve and enhance the removal of stomach contents, which, in turn, may improve contact between gastric mucosa and the heat transfer region 102 of the reinforced heat transfer device 100. Such improved contact may enhance heat transfer between the reinforced heat transfer device 100 and the gastric mucosa and, thus, enhance heating or cooling of the subject. The configuration of the ports 130 shown in FIG. 1 is oval. However, the ports 130 can be, for example, circular, rectangular, or any other shape that permits flow of gastric contents from the stomach to the gastric access lumen 128.

The reinforced heat transfer device 100 is manufactured via, for example, extrusion. For example, utilizing extrusion processes to form the reinforced heat transfer device 100 may eliminate the need to seal junctions or affix end caps and reduce the points at which leaks may occur. In some examples, the flexible tubing 124, the wall 118, and the gastric access tube 126 are integrally formed via extrusion. In other examples, the flexible tubing 124 and the wall 118 are integrally formed via extrusion, the gastric access tube 126 is formed separately via extrusion, and the gastric access tube 126 is subsequently inserted into the internal cavity 104 defined by the flexible tubing 124. In other examples, the flexible tubing 124, the wall 118, and the gastric access tube 126 are formed separately via extrusion, and the wall 118 and the gastric access tube 126 are inserted into the internal cavity 104 to assemble the reinforced heat transfer device 100.

In some examples, components of the reinforced heat transfer device 100 (e.g., the flexible tubing 124, the wall 118, and the gastric access tube 126) includes or is formed of a semi-rigid material such as a semi-rigid polymer. For example, the flexible tubing 124, the wall 118, and/or the gastric access tube 126 is formed of silicone to increase a flexibility and/or a thermal conductivity of the reinforced heat transfer device 100. In some such examples, the components of the reinforced heat transfer device 100 are formed of biomedical grade extruded silicone rubber such as Dow Corning Q7 4765 silicone. When the flexible tubing 124 is formed of silicone, the heat transfer region 102 defined by the flexible tubing 124 more efficiently transfers heat from the heat transfer medium to the esophageal epithelium to heat or cool the subject due to the increased thermal conductivity of the material forming the reinforced heat transfer device 100. In other examples, the components of the reinforced heat transfer device 100 are formed of other semi-rigid materials including semi-rigid plastics such as ethylene tetrafluoroethylene (ETFE), polytetrafluoroethylene (PTFE), perfluoroalkoxy (PFA), and fluorinated ethylene propylene (FEP).

In certain embodiments, the reinforced heat transfer device 100 of the illustrated example includes one or more reinforcing elements disposed within one or more lumens, such as an inflow lumen and/or an outflow lumen.

In certain embodiments, the reinforced heat transfer device 100 of the illustrated example includes one or more reinforcing elements, such as a reinforcing wire (e.g., mesh, coil), embedded into the flexible tubing 124, the wall 118, and/or the gastric access tube 126 of the reinforced heat transfer device 100. For example, a reinforcing wire may be embedded into one or more of the components of the reinforced heat transfer device 100 during the extrusion process. The reinforcing wire may be a metallic wire that stiffens the reinforced heat transfer device 100. In some such embodiments, the reinforcing wires form a mesh embedded in the flexible tubing 124, a mesh embedded in the wall 118, and/or a mesh embedded in the gastric access tube 126 of the to reinforce the semi-rigid material of the reinforced heat transfer device 100. In other examples, the reinforcing wires may be springs (e.g., helical springs such as 5-millimeter helical springs, D-shaped springs) that are embedded in the flexible tubing 124, the wall 118, and/or the gastric access tube 126 to reinforce or stiffen the reinforced heat transfer device 100.

In certain embodiments, the reinforced heat transfer device 100 includes a reinforcing element, such as a reinforcing wire, to prevent the fluid path from becoming blocked when a negative pressure is applied to the heat transfer medium supply lumen 114 and/or the heat transfer medium return lumen 116.

For example, the heat transfer device 100 may be fluidly connected to a heat exchanger via the inlet port 110 and the outlet port 112 to enable the heat transfer device 100 to transfer heat to heat or cool the subject. In some examples, the heat exchanger provides the heat transfer medium to the heat transfer device 100 by creating a negative pressure. In some instances, when the flexible tubing 124, the wall 118, and/or the gastric access tube 126 defining the heat transfer medium supply lumen 114 and/or the heat transfer medium return lumen 116 are formed of silicone rubber and/or any other semi-rigid material without a reinforcing element, the negative pressure generated by the heat exchanger potentially may cause the flexible tubing that defines the heat transfer medium supply lumen 114 and/or the heat transfer medium return lumen 116 to collapse. In such instances, the heat transfer medium is unable to flow through the fluid path defined by the heat transfer medium supply lumen 114 and the heat transfer medium return lumen 116 and, thus, is unable to cause heat to transfer to the subject via the heat transfer region 102.

The reinforcing element of the heat transfer device 100 serves to stiffen and/or otherwise reinforce the flexible tubing 124, the wall 118, and/or the gastric access tube 126 to prevent the heat transfer medium supply lumen 114 and the heat transfer medium return lumen 116 from collapsing when negative pressure is created by the heat exchanger fluidly connected to the heat transfer device 100. That is, the reinforcing element facilitates flow of the heat transfer medium through the fluid path of the heat transfer device 100 when utilized with an external heat exchanger that provides heat transfer medium via negative pressure, thereby enabling the heat transfer device 100 to be utilized with such heat exchangers to warm or cool a subject.

In certain embodiments, a reinforcing element, such as one formed of metallic material(s), increases radio-opacity of the heat transfer device 100. For example, the increased radio-opacity enables the heat transfer device 100 to be viewed via an x-ray when inserted into the esophagus of the subject. By enabling the heat transfer device 100 to be viewed via an x-ray, the reinforcing element enables an operator (e.g., a technician, a nurse, a doctor) to utilize an x-ray to determine a location of and/or to navigate the heat transfer device 100 when inserted into the subject.

Figure 4:
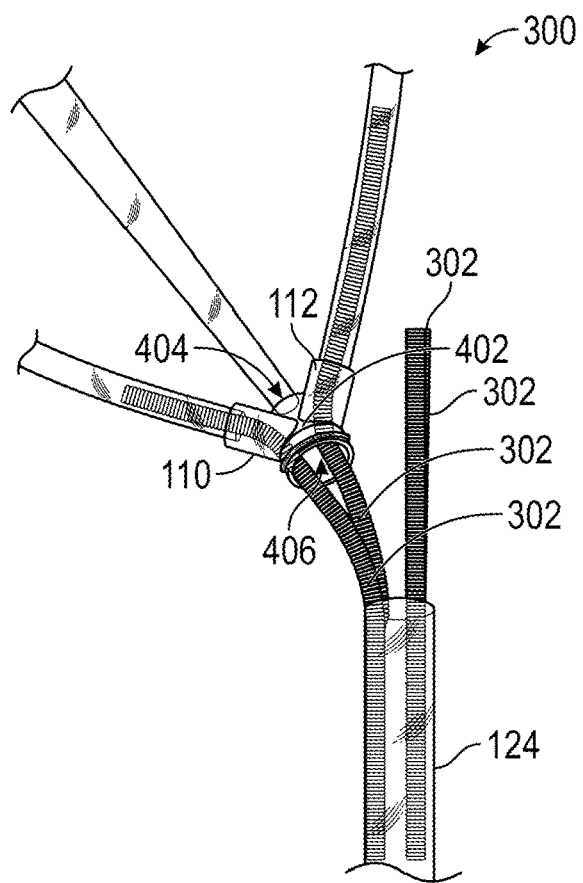
FIG. 4 depicts portions of reinforcing springs extending through the heat transfer device of FIGS. 3A and 3B.
Figure 5:
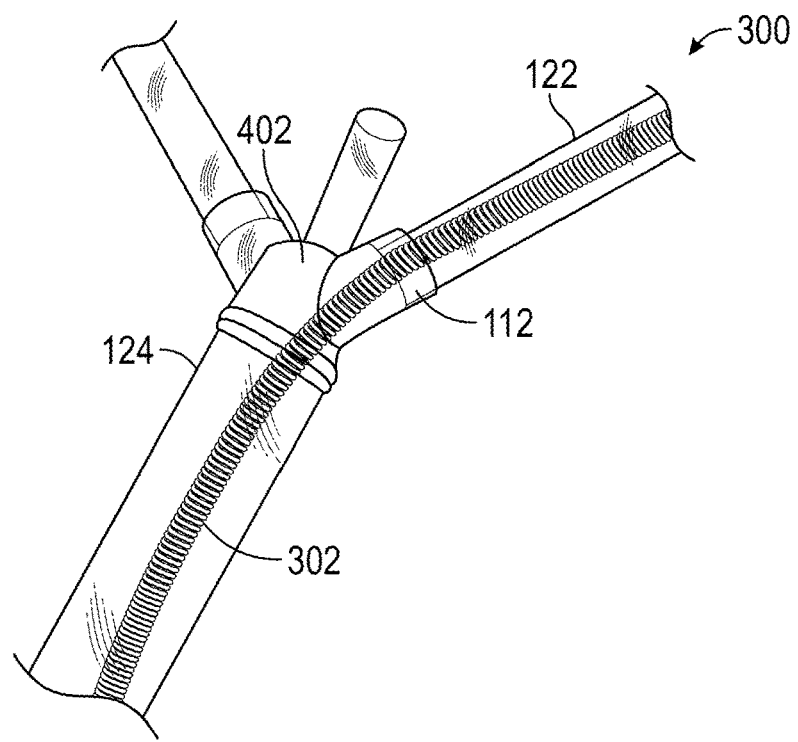
FIG. 5 further depicts a portion of one of the reinforcing springs extending through the heat transfer device of FIGS. 3A and 3B.

FIGS. 3A, 3B, 4, and 5 illustrate another example heat transfer device 300 in accordance with the teachings herein. More specifically, FIG. 3 depicts the heat transfer device 300 when assembled, FIG. 4 depicts a cross-sectional top view of the heat transfer device 300, FIG. 5 depicts a portion of the heat transfer device 300 when partially disassembled, and FIG. 6 depicts a portion of the heat transfer device 300 when partially assembled.

As illustrated in FIGS. 3A and 3B, the heat transfer device 300 includes the heat transfer region 102, the proximal end 106, the distal end 108, the inlet port 110, the outlet port 112, the wall 118, and the gastric access tube 126. Those components of the heat transfer device 300 are identical to or substantially similar to the heat transfer region 102, the proximal end 106, the distal end 108, the inlet port 110, the outlet port 112, the wall 118, and the gastric access tube 126 as disclosed in accordance with FIGS. 1-2. Accordingly, some features of those components of the heat transfer device 300 will not be described in further detail below.

The heat transfer device 300 includes one or more reinforcing elements 302 that extend through the internal cavity 104 to reinforce or stiffen the heat transfer device 300. In certain embodiments, the reinforcing element(s) 302 are metallic wires that stiffen the reinforced heat transfer device 300. As illustrated in FIG. 3A, one or more of the reinforcing elements 302 extend through the inlet port 110 and/or into the inflow tube 120 to reinforce at least a portion of the inflow tube 120. One or more of the reinforcing elements 302 also extend through the outlet port 112 and/or into the outflow tube 122 to reinforce at least a portion of the outflow tube 122.

As illustrated in FIG. 3B, one or more of the reinforcing elements 302 are inserted into the heat transfer medium supply lumen 114 to reinforce the heat transfer medium supply lumen 114 to prevent the heat transfer medium supply lumen 114 from collapsing when a negative pressure is applied. Further, one or more of the reinforcing elements 302 are inserted into the heat transfer medium return lumen 116 to reinforce the heat transfer medium return lumen 116 to prevent the heat transfer medium return lumen 116 from collapsing when a negative pressure is applied. In the illustrated example, two of the reinforcing elements 302 are inserted into the heat transfer medium supply lumen 114, and two of the reinforcing elements 302 are inserted into the heat transfer medium return lumen 116. In other examples, more or less of the reinforcing elements 302 may be inserted into the heat transfer medium supply lumen 114 and/or the heat transfer medium return lumen 116 to stiffen the heat transfer device 300. Further, in some examples, one or more of the reinforcing elements 302 are inserted into the gastric access lumen 128.

In the illustrated example, the reinforcing elements 302 are springs, such as helical springs (e.g., 5-millimeter helical springs) or D-shaped springs. In other examples, the reinforcing elements 302 are meshes that extend through the internal cavity 104 of the heat transfer device 300. Further, in the illustrated example, the flexible tubing 124, the wall 118, and/or the gastric access tube 126 are not embedded with reinforcing wires such that the reinforcing elements 302 inserted into the internal cavity 104 to prevent the flexible tubing 124, the wall 118, and/or the gastric access tube 126 from collapsing. In other examples, other reinforcing elements (e.g., a reinforcing wire) are embedded into the flexible tubing 124, the wall 118, and/or the gastric access tube 126 such that the reinforcing element and the embedded reinforcing wires combine to reinforce the fluid path of the heat transfer device 300.

FIG. 4 illustrates a portion of the heat transfer device 300 when a port connector 402 of the heat transfer device 300 is decoupled from the flexible tubing 124. As illustrated in FIG. 4, the port connector 402 includes the inlet port 110, the outlet port 112, an aperture 404 through which the gastric access tube 126 is to extend, and an end 406 that is to couple to the flexible tubing 124. In the illustrated example, two reinforcing elements 302 extend through the heat transfer medium supply lumen 114. Additionally, two reinforcing elements 302 extend through the heat transfer medium return lumen 116.

FIG. 5 illustrates a portion of the heat transfer device 300 when the port connector 402 is coupled to the flexible tubing 124 of the heat transfer device 300. In the illustrated example, one reinforcing element 302 extends through the heat transfer medium return lumen 116, through the outlet port 112, and at least partially into the outflow tube 122.

Additional Embodiments

In one aspect, the present disclosure provides an esophageal heat transfer device comprising at least one reinforced tube defining a lumen for flow of a heat transfer medium. In certain embodiments, the reinforced tube is a silicone tube.

In one aspect, the present disclosure provides an esophageal heat transfer device comprising a lumen for flow of a heat transfer medium and a reinforcing element disposed within said lumen. In certain embodiments, the reinforcing element is a coil, preferably a spring, and more preferably a metal spring.

In one aspect, the present disclosure provides an esophageal heat transfer device comprising a first reinforced tube defining an inflow lumen and a second reinforced tube defining an outflow lumen. In certain embodiments, the first and second reinforced tubes have sufficient radial strength to prevent collapse in a negative pressure environment.

In one aspect, the present disclosure provides an esophageal heat transfer device comprising an inflow lumen in fluid communication with an outflow lumen, and at least one reinforcing element disposed within said inflow lumen or said outflow lumen. In certain embodiments, at least one reinforcing element is disposed within each of said inflow lumen and said outflow lumen.

In one aspect, the present disclosure provides a reinforced esophageal heat transfer device comprising: (a) a distal end configured for nasopharyngeal or oropharyngeal insertion into an esophagus of a subject; (b) a proximal end including an inlet port and an outlet port; (c) a heat transfer region between the distal end and the proximal end; (d) one or more lumens configured for providing a fluid path for flow of a heat transfer medium to and from the heat transfer region; and (e) one or more reinforcing elements configured for reinforcing the one or more lumens to enable the heat transfer medium to flow through the fluid path via negative pressure.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

What is claimed is:

1. A reinforced esophageal heat transfer device comprising:
   a distal end configured for nasopharyngeal or oropharyngeal insertion into an esophagus of a subject;
   a proximal end including an inlet tube and an outlet tube;
   a heat transfer region between the distal end and the proximal end;
   a heat transfer medium supply lumen for providing a supply fluid path for flow of a heat transfer medium to and through the heat transfer region, the heat transfer medium supply lumen being connected to the inlet tube;
   a heat transfer medium return lumen for providing a return fluid path for flow of the heat transfer medium through and from the heat transfer region, the heat transfer medium return lumen being connected to the outlet tube;
   a gastric access lumen passing through the heat transfer region and disposed parallel to the heat transfer medium supply lumen and the heat transfer medium return lumen, the gastric access lumen configured to allow gastric decompression or drainage, wherein each of the heat transfer medium supply lumen, the heat transfer medium return lumen, and the gastric access lumen are separated from each of the other two lumens by at least one internal wall; and
   a pair of metal reinforcing return coils that are arranged in parallel within the outlet tube and the heat transfer medium return lumen and that are configured for reinforcing the outlet tube and the heat transfer medium return lumen to enable the heat transfer medium to flow through the return fluid path via negative pressure applied to the outlet tube.

2. The reinforced esophageal heat transfer device of claim 1, wherein the heat transfer medium return lumen is separated from the heat transfer medium supply lumen by two internal walls, and the gastric access lumen is located between the heat transfer medium return lumen and the heat transfer medium supply lumen.

3. The reinforced esophageal heat transfer device of claim 2, further including a pair of metal reinforcing supply coils that are arranged in parallel within the inlet tube and the heat transfer medium supply lumen and that are configured for reinforcing the inlet tube and the heat transfer medium supply lumen to enable the heat transfer medium to flow through the supply fluid path via negative pressure applied to the outlet tube.

4. The reinforced esophageal heat transfer device of claim 1, further including a pair of metal reinforcing supply coils that are arranged in parallel within the inlet tube and the heat transfer medium supply lumen and that are configured for reinforcing the inlet tube and the heat transfer medium supply lumen to enable the heat transfer medium to flow through the supply fluid path via negative pressure applied to the outlet tube.

5. A method for controlling core body temperature in a subject in need thereof, the method comprising the steps of:
   providing the heat transfer device according to claim 1;
   placing the heat transfer region of the heat transfer device in an esophagus of the subject; and
   initiating flow of the heat transfer medium along the fluid path by applying a negative pressure to the outlet tube.

* * * * *